US009771196B1

(12) United States Patent
Speed et al.

(10) Patent No.: US 9,771,196 B1
(45) Date of Patent: Sep. 26, 2017

(54) DENTAL MAINTENANCE KIT

(76) Inventors: Terri Lynn Speed, Elk Grove, CA (US); Marvin Ernest Speed, II, Elk Grove, CA (US)

(*) Notice: Subject to any disclaimer, the term of this patent is extended or adjusted under 35 U.S.C. 154(b) by 616 days.

(21) Appl. No.: 12/931,203

(22) Filed: Jan. 25, 2011

(51) Int. Cl.
*B65D 69/00* (2006.01)
*A61C 19/02* (2006.01)
*A45C 11/00* (2006.01)

(52) U.S. Cl.
CPC ........... *B65D 69/00* (2013.01); *A45C 11/008* (2013.01); *A61C 19/02* (2013.01)

(58) Field of Classification Search
CPC ........ B65D 69/00; A61C 19/02; A45C 11/008
USPC .............. 206/63.5, 223, 570, 572, 581, 229; 132/309; 433/31, 46, 143, 146
See application file for complete search history.

(56) References Cited

U.S. PATENT DOCUMENTS

| 1,684,417 | A | * | 9/1928 | Silberman | 206/229 |
| 3,366,230 | A | * | 1/1968 | Loran | 206/63.5 |
| 3,921,649 | A | * | 11/1975 | Milbrath | 132/308 |
| 4,293,074 | A | * | 10/1981 | Dunsky | 206/572 |
| 4,828,113 | A | * | 5/1989 | Friedland et al. | 206/570 |
| 5,217,372 | A | * | 6/1993 | Truocchio | 433/215 |
| 5,626,227 | A | * | 5/1997 | Wagner et al. | 206/369 |
| 6,102,051 | A | * | 8/2000 | Neves | 132/321 |
| 6,109,918 | A | * | 8/2000 | Hammond et al. | 433/141 |
| 6,199,457 | B1 | * | 3/2001 | Hoff et al. | 81/177.85 |
| 6,206,192 | B1 | * | 3/2001 | Winstead et al. | 206/572 |
| 6,247,477 | B1 | * | 6/2001 | Wagner | 132/309 |
| 6,322,362 | B1 | * | 11/2001 | Holms | 433/143 |
| 6,729,877 | B2 | * | 5/2004 | Rahman | 433/141 |
| 6,905,335 | B2 | * | 6/2005 | Fischer | 433/77 |
| 2004/0038176 | A1 | * | 2/2004 | Hallows | 433/141 |
| 2004/0187888 | A1 | * | 9/2004 | Vandyke | 132/309 |
| 2006/0027246 | A1 | * | 2/2006 | Wilkinson | 132/309 |
| 2006/0110701 | A1 | * | 5/2006 | Cwik | 433/31 |
| 2008/0227051 | A1 | * | 9/2008 | Szwajkowski et al. | 433/24 |

* cited by examiner

Primary Examiner — Anthony Stashick
Assistant Examiner — Ernesto Grano
(74) Attorney, Agent, or Firm — Risto A. Rinne, Jr

(57) ABSTRACT

A dental maintenance kit for the removal of stains and debris from the surface and from between the teeth that includes an intraoral tool equipped with a detachably-attachable sickle blade and scaler blade. A preferred material for the intraoral tool is non-metallic that includes a recess at each opposite end of the intraoral tool for acceptance of a protrusion on the non-working end of the sickle blade and or the scaler blade. The protrusion will have means to secure the sickle blade or scaler blade firmly into the recess at each opposite end of the intraoral tool. A preferred material for the sickle blade and scaler blade is stainless steel. A coating is applied to a shaft of the sickle blade or scaler blade that extends longitudinally for the entire length of the shaft exposing only the working surface of the sickle blade or scaler blade. A preferred material for the coating is non-metallic. A guide is included with the dental maintenance kit. The guide provides written instructions for the use of the intraoral tool included in the dental maintenance kit.

18 Claims, 8 Drawing Sheets

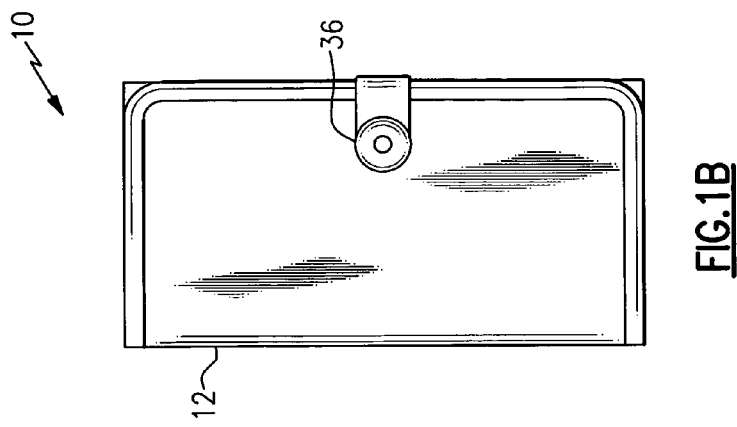
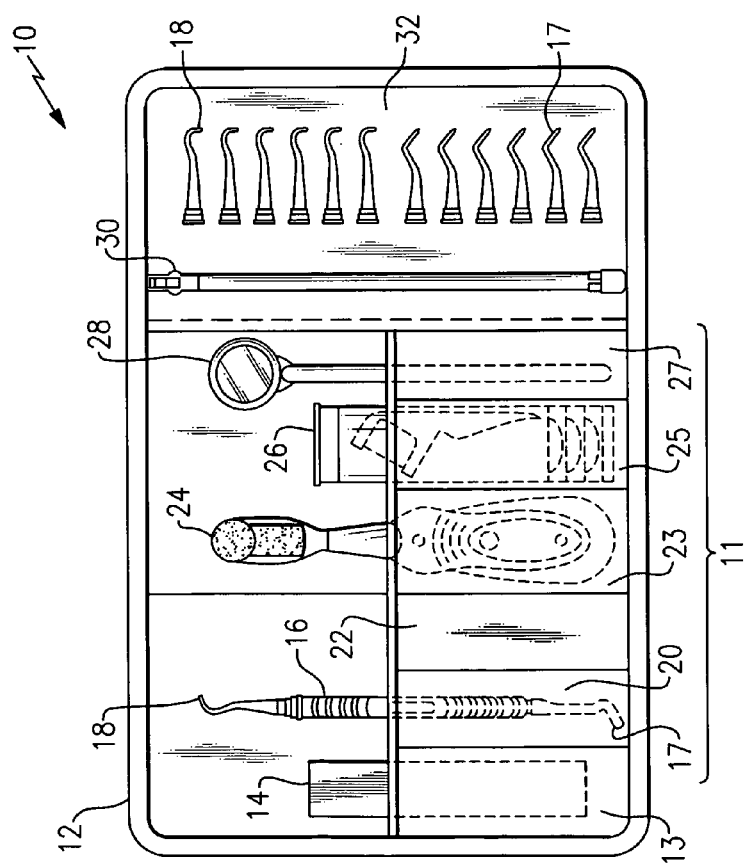

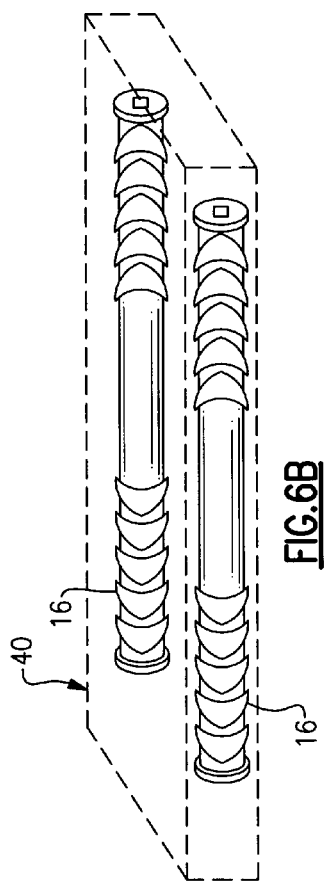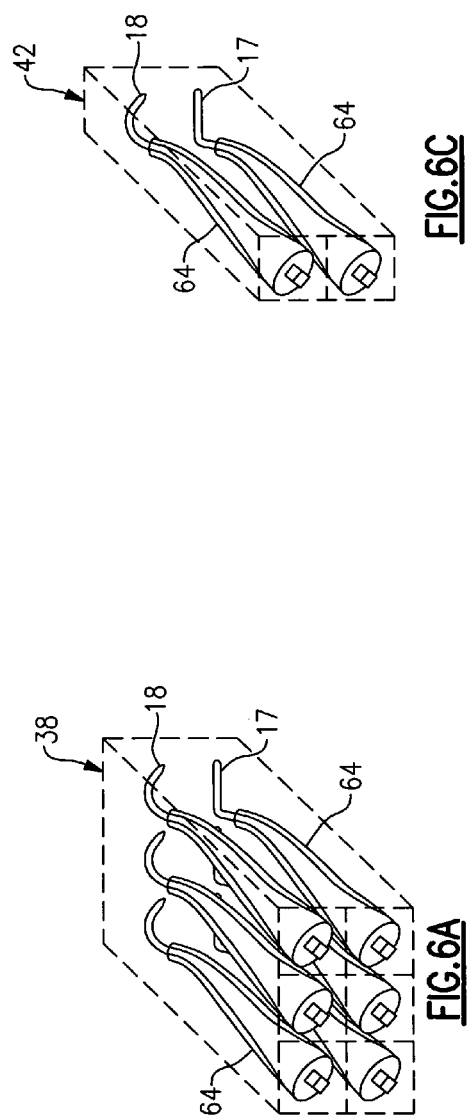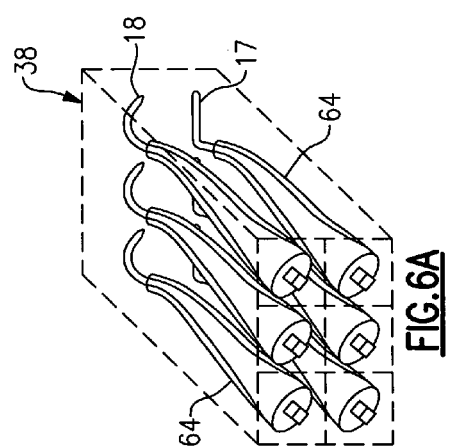

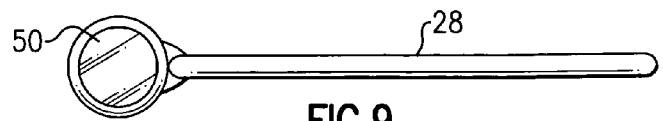
FIG.9
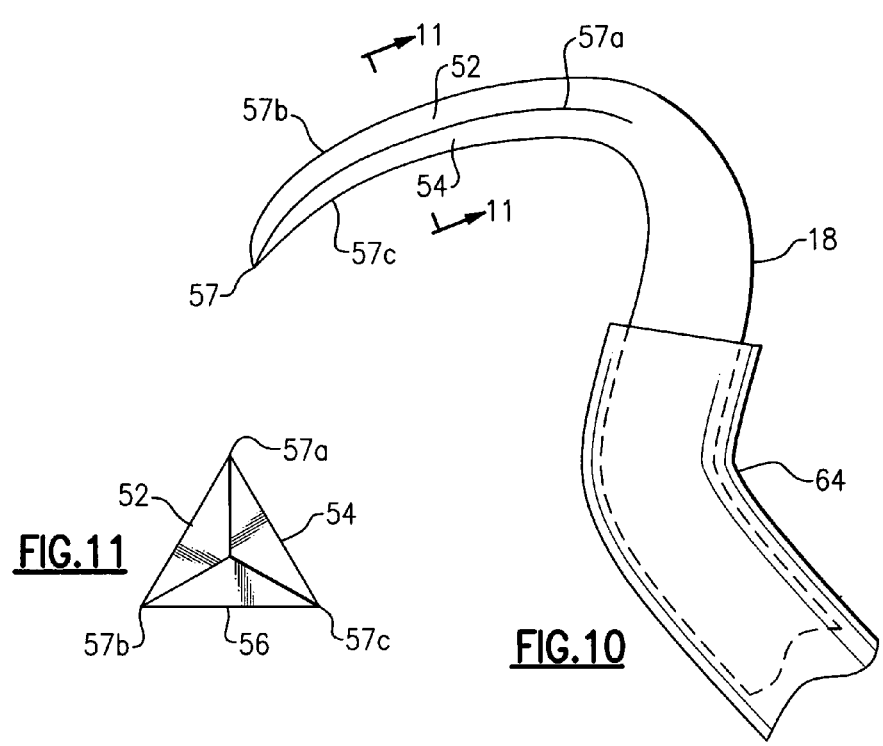
FIG.11
FIG.10
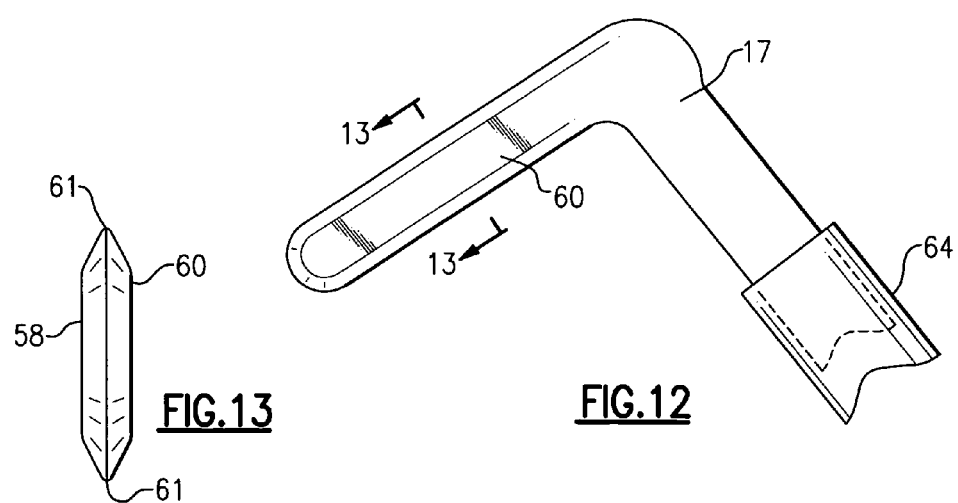
FIG.13
FIG.12

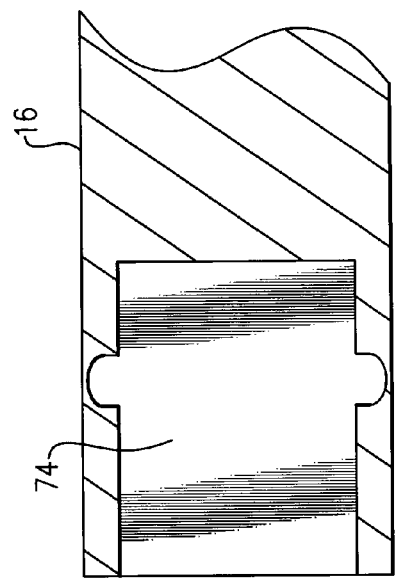
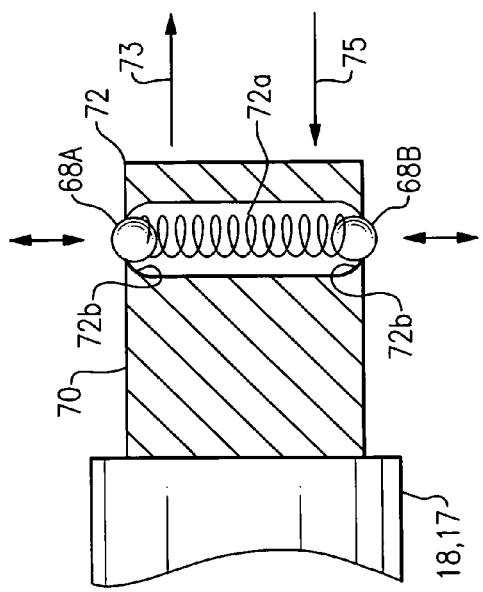

DENTAL MAINTENANCE KIT

BACKGROUND OF THE INVENTION

1. Field of the Invention

The present invention, in general, relates to dentistry and, more particularly, to dental prophylaxis.

The American Dental Association recommends that individuals have a dental exam and cleaning at least once per year. People with more specialized needs may require an examination or cleaning more frequently, such as every 3 months, 6 months, or other interval. The regular cleaning and removal of plaque is known to reduce the possibility of developing gum disease.

One of the problems relating to regularly scheduled appointments is that some people are unable to regularly schedule appointments for various reasons such as time, availability, financial limitations, or their being in college or on vacation. There remains a need to remove plaque and stains for aesthetic reasons and also to help prevent gum disease and inflammation. Common methods for cleaning teeth and gums such as a toothbrush or floss have proven to be ineffective at removing plaque and dental stains. Currently available travel products in the market are generally equipped with a toothbrush, toothpaste, and perhaps floss. These are ineffective in removing plaque, dental stains, and certain types of debris which may become lodged between teeth or under a crown that normal brushing and flossing activities are unable to remove, which can lead to scheduling an appointment with a dentist to remove the aforementioned debris and plaque.

Accordingly, there exists today a need for a dental maintenance kit that helps to ameliorate the above-mentioned problems and difficulties as well as ameliorate those additional problems and difficulties as may be recited in the "OBJECTS AND SUMMARY OF THE INVENTION" or discussed elsewhere in the specification or which may otherwise exist or occur and that are not specifically mentioned herein.

As various embodiments of the instant invention help provide a more elegant solution to the various problems and difficulties as mentioned herein, or which may otherwise exist or occur and are not specifically mentioned herein, and by a showing that a similar benefit is not available by mere reliance upon the teachings of relevant prior art, the instant invention attests to its novelty. Therefore, by helping to provide a more elegant solution to various needs, some of which may be long-standing in nature, the instant invention further attests that the elements thereof, in combination as claimed, cannot be obvious in light of the teachings of the prior art to a person of ordinary skill and creativity.

Clearly, a dental maintenance kit would be useful and desirable.

2. Description of Prior Art

Dental maintenance is in general known. For example, toothbrush and toothpaste kits are known. These kits are designed to address superficial and cosmetic teeth cleaning. These kits do not include a specific selection of tools and materials that enable a user to perform a more comprehensive cleaning or remove debris or particles from between teeth which may cause discomfort or inflammation.

While the structural arrangements of the above described devices may, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a dental maintenance kit that permits people to perform dental prophylaxis between regularly scheduled visits.

It is also an important object of the invention to provide a dental maintenance kit that helps to remove stains from teeth such as stains originating from coffee, tea, and other common sources of teeth discoloration.

Another object of the invention is to provide a dental maintenance kit that includes an intraoral tool.

Still another object of the invention is to provide a dental maintenance kit that can be used to remove debris that is embedded between teeth.

Still yet another object of the invention is to provide a dental maintenance kit that includes an intraoral tool which includes removable and replaceable blades.

Yet another important object of the invention is to provide a dental maintenance kit that includes an intraoral tool which includes blades with a release feature that allows the blades to detach from the handle if excessive force is applied during use.

A first continuing object of the invention is to provide a dental maintenance kit that includes a plastic coating at a base portion of a sickle or a scaler blade which only exposes a tip of the blade to prevent injury to a user.

A second continuing object of the invention is to provide a dental maintenance kit that includes a detachable dental blade that has a protrusion which fits within a recess provided in a plastic handle of an intraoral tool to secure the blade to the intraoral tool.

A third continuing object of the invention is to provide a dental maintenance kit that includes an intraoral tool and at least one sickle blade and at least one scaler blade for attachment thereto.

A fourth continuing object of the invention is to provide a dental maintenance kit that includes a detachable dental blade that has a mounting mechanism which acts as a safety release if an intraoral tool is subjected to excess prying of pulling pressure.

A fifth continuing object of the invention is to provide a dental maintenance kit that includes a battery powered toothbrush with rotary bristles.

A sixth continuing object of the invention is to provide a dental maintenance kit that includes easily understood printed instructions.

A seventh continuing object of the invention is to provide a dental maintenance kit that is designed for easy and safe usage by an unskilled user.

An eighth continuing object of the invention is to provide a dental maintenance kit that includes a standard dental mirror.

A ninth continuing object of the invention is to provide a dental maintenance kit that includes a dental pumice paste.

A tenth continuing object of the invention is to provide a dental maintenance kit that includes specialized tools which allow for comprehensive plaque and debris removal.

An eleventh continuing object of the invention is to provide a dental maintenance kit that includes a toothbrush and flossing tool for routine dental cleaning between meals.

A twelfth continuing object of the invention is to provide a dental maintenance kit that is portable.

A thirteenth continuing object of the invention is to provide a dental maintenance kit that is compact.

A fourteenth continuing object of the invention is to provide a dental maintenance kit that includes an intraoral tool with blades which can be replaced when they are damaged or become dull or, if desired, when a different type of blade is preferred.

A fifteenth continuing object of the invention is to provide a dental maintenance kit that includes an intraoral tool with a plastic safety coating on a base and non-working areas of a sickle and a scaler blade.

A sixteenth continuing object of the invention is to provide a dental maintenance kit that provides an affordable solution for dental care between regularly scheduled dentist appointments.

A seventeenth continuing object of the invention is to provide a dental maintenance kit that reduces dental expenses relating to additional appointments which may occur to address urgent dental needs that may occur between regularly scheduled dental appointments.

An eighteenth continuing object of the invention is to provide a dental maintenance kit that helps to address dental needs which may occur while traveling.

A nineteenth continuing object of the invention is to provide a dental maintenance kit that includes a dental prophylaxis tool for the performance of dental intraoral maintenance between regularly scheduled dental appointments that is inexpensive and easily portable.

Briefly, a dental maintenance kit that is constructed in accordance with the principles of the present invention preferably has a pouch that is foldable and subdivided into individual pockets. The dental maintenance kit includes an intraoral tool. The intraoral tool includes a longitudinal body and means at opposite ends of the body for the insertion and removal of a replaceable blade at each end. The body of the intraoral tool functions as a handle during use. At least one sickle blade and at least one scaler blade are included. Additional blades may be included with the kit. An instructional guide is provided to teach an unskilled user how to safely use the intraoral tool. A pocket with a zipper is preferably provided to contain one or more optional spare blades for the intraoral tool body. The pouch is preferably foldable at mid point with a button snap to secure the pouch from unintentional opening. Other optional components are also described.

BRIEF DESCRIPTION OF THE DRAWINGS

FIG. 1A is a top view of a dental maintenance kit with a storage pouch shown in an open orientation with a plurality of components therein.

FIG. 1B is a side view of the dental maintenance kit of FIG. 1A that shows the pouch in a closed orientation.

FIG. 6A is a view in perspective of a packaging option for the purchase of additional or replacement blades consisting of three sickle blades and three scaler blades.

FIG. 6B is a view in perspective of a packaging option for the purchase of additional or replacement intraoral tools consisting of two intraoral tools.

FIG. 6C is a view in perspective of a packaging option for the purchase of an additional or replacement sickle blade and scaler blade.

FIG. 9 is a top view of a standard type dental mirror for inclusion with the dental maintenance kit of FIG. 1A.

FIG. 10 is a partial side view of a sickle blade for attachment to an intraoral tool of the dental maintenance kit of FIG. 1A.

FIG. 11 is a cross sectional view taken along the line 11-11 in FIG. 10.

FIG. 12 is a partial side view of a scaler blade for attachment to an intraoral tool of the dental maintenance kit of FIG. 1A.

FIG. 13 is a cross sectional view taken along the line 13-13 in FIG. 12.

FIG. 16A is a cross sectional view taken on the line 16A-16A in FIG. 14 of a locking mechanism incorporated into a protrusion located at the base of each sickle (or scaler) blade.

FIG. 16B is a cross sectional view of a receiver taken on the line 16B-16B in FIG. 15 of the intraoral tool of the dental maintenance kit of FIG. 1A.

DETAILED DESCRIPTION OF THE INVENTION

Figure 2:
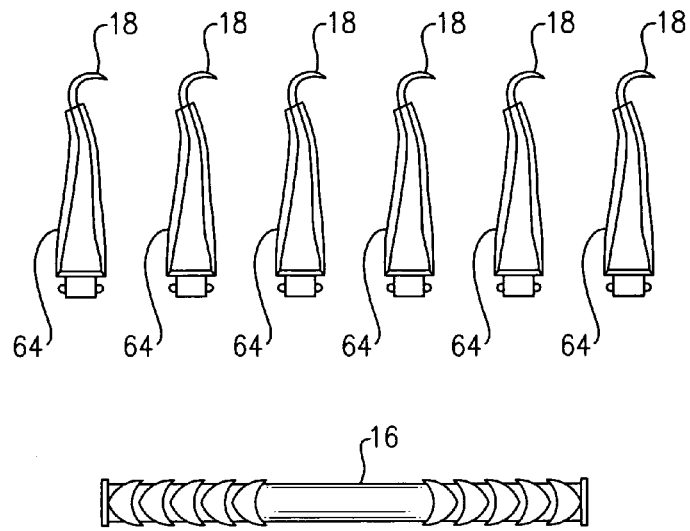
FIG. 2 is a side view of an intraoral tool of the dental maintenance kit of FIG. 1A and a plurality of sickle blades.

Referring on occasion to all of the FIGURE drawings and now, in particular to FIG. 1A, is shown a dental maintenance kit, identified in general, by the reference numeral 10.

The reader will notice that reference is occasionally made throughout the DETAILED DESCRIPTION OF THE INVENTION suggesting that the reader refer to a particular drawing FIGURE. The suggestion is at times made when the introduction of a new element requires the reader to refer to a different drawing FIGURE than the one currently being viewed and also when the timely viewing of another drawing FIGURE is believed to significantly improve ease of reading or enhance understanding. To promote rapid understanding of the instant invention the reader is encouraged to periodically refer to and review each of the drawing FIGURES for possible cross-referencing of component parts and for other potentially useful information.

The dental maintenance kit 10 is for the performance of routine dental care when a person (i.e., user) is unable to have a normal dental cleaning and examination. The dental maintenance kit 10 is not intended to replace regular dental examinations or regular dental hygiene (prophylaxis) appointments. The dental maintenance kit 10 includes a pouch 12. The pouch 12 includes a plurality of pockets, identified by bracket 11, for the purpose of organizing and storage of the component parts that make up the dental maintenance kit 10. The specific component parts are described in greater detail hereafter. The arrangement of the plurality of pockets 11 can vary as desired, providing that each of the plurality of pockets 11 is of sufficient size and shape to accept a specific component part.

The plurality of pockets 11 includes a first pocket 13. The first pocket 13, as shown, is used for storage of a guide 14. The guide 14 provides instructions and guidelines for proper use of the dental maintenance kit 10. The guide 14 will include instructions for proper use of all of the component parts and, in particular, for use of an intraoral tool 16.

An adjacent second pocket 20 is disposed to the right of the first pocket 13. The second pocket 20 is for storage of the intraoral tool 16. The second pocket 20 is sized to accept the preferred basic configuration of the intraoral tool 16 that includes a sickle blade 18 and a scaler blade 17 attached at the opposite ends of the intraoral tool 16.

A third pocket 22, to the right of the second pocket 20, as shown, is a pocket without a specific component designated for storage therein. The pocket 22 may be used for storage of additional components as are described in greater detail hereafter.

A fourth pocket 23 is disposed to the right of the third pocket 22. The fourth pocket 23 is utilized for storage of a toothbrush 24. The toothbrush 24 is described in greater detail hereinafter.

A fifth pocket 25 is disposed to the right of and adjacent to the fourth pocket 23. The fifth pocket 25 is utilized for the storage of a plurality of components 26 (see FIG. 1) that are preferably stored in a plastic container 48 (see FIG. 8). The plastic container 48 within this fifth pocket 25 contains (see FIG. 8) a flossing tool 44, a quantity of floss 45, and three containers of dental pumice paste 46. The flossing components are described in greater detail hereinafter.

A sixth pocket 27 is disposed to the right of the fifth pocket 25 for the storage of a standard type of dental mirror 28.

A seventh pocket 32 is disposed to the right of the sixth pocket 27 for the storage of extra sickle blades 18 and extra scaler blades 17. The seventh pocket 32 preferably includes a zipper 30 to prevent the loss of spare sickle blades 18 or spare scaler blades 17, if the spare blades 17, 18 are included in the dental maintenance kit 10 or are purchased later.

Referring to FIG. 1B, the storage pouch 12 is shown in a closed position. The pouch 12, while in the closed position is folded and secured with a snap button 36 to prevent unintentional opening that can lead to a loss of components. Of course numerous variations in the design of the pouch 12 are possible. If desired, VELCRO' could be used to secure the pouch 12 in the closed position. A zipper closure (not shown) is also possible.

The dental maintenance kit 10 is comprised of dental components and parts that have been selected to work in conjunction with each other to provide options for regular cleaning between meals and, when desired, a more comprehensive cleaning.

Referring to FIG. 2, a side view of a plurality of the sickle blades 18 and a side view of the intraoral tool 16 is shown. The sickle blades 18 are secured to the intraoral tool 16, utilizing a locking mechanism that is described in greater detail hereafter.

Figure 3:
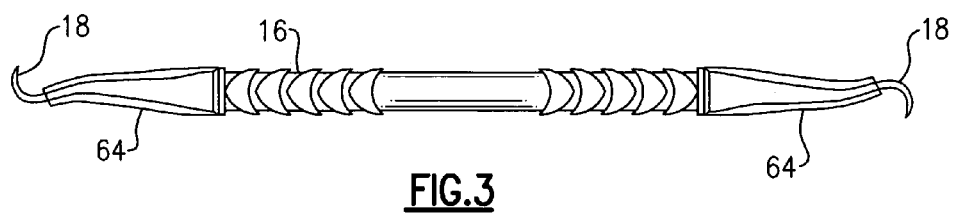
FIG. 3 is a side view of the intraoral tool of the dental maintenance kit of FIG. 1A with a sickle blade attached at each end, thereof.

Referring to FIG. 3, the intraoral tool 16 is shown with the sickle blade 18 attached at each end of the intraoral tool 16. At a minimum one sickle blade 18 and one scaler blade 17 are included in the dental maintenance kit 10. If the blades 17, 18 are included or are purchased later, a user may attach the sickle blade 18 at one end of the intraoral tool 16 and the scaler blade 17 at the opposite end or the user may wish to attach two of the same type of blade 17, 18 at opposite ends.

Figure 4:
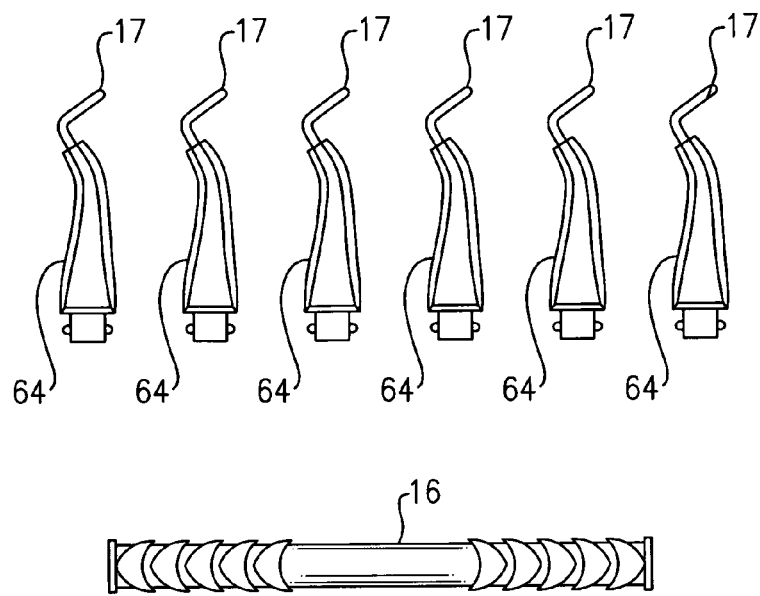
FIG. 4 is a side view of the intraoral tool of the dental maintenance kit of FIG. 1A and a plurality of scaler blades.

Referring to FIG. 4, is shown a side view of the plurality of scaler blades 17 and the intraoral tool 16. The scaler blades 17 are attached to the intraoral tool 16 with the locking mechanism, as briefly mentioned above, for the attachment of the sickle blade 18.

Figure 5:
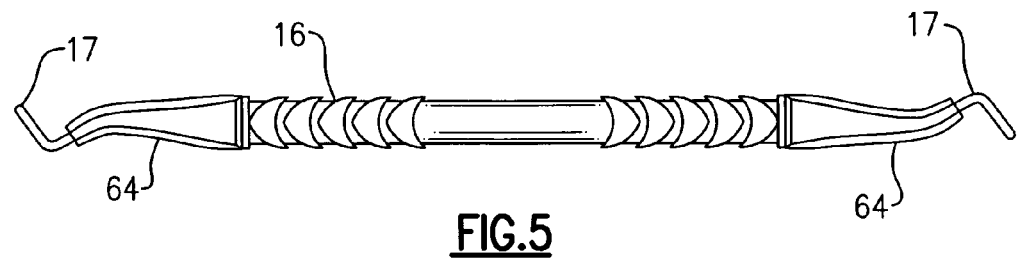
FIG. 5 is a side view of the intraoral tool of the dental maintenance kit of FIG. 1A with a scaler blade attached at each end, thereof.

Referring to FIG. 5, a side view of the intraoral tool 16 is shown with the scaler blade 17 attached at each end of the intraoral tool 16. As mentioned earlier, the minimal preferred intraoral tool 16 configuration is the sickle blade 18 and the scaler blade 17 attached at each opposite end of the intraoral tool 16 as shown in FIG. 1A. In general, the sickle blade 18 is often preferred for cleaning between teeth and the scaler blade 17 is often preferred for cleaning the teeth surfaces. Detailed safe cleaning instructions are provided in the instruction guide 14.

Referring to FIG. 6A, a packaging option, identified in general by reference numeral 38, is shown that includes three replacement sickle blades 18 and three replacement scaler blades 17. Referring to FIG. 6B, a packaging option, identified in general by reference numeral 40, for two replacement intraoral tools 16 is shown. The intraoral tool 16 is preferably made of plastic to keep cost and weight down. It also makes the dental maintenance kit 10 less likely to be detected at airport security screening stations. Referring to FIG. 6C, a packaging option, identified in general by reference numeral 42, for a single sickle blade 18, and a single scaler blade 17 is shown. These are shown to illustrate how replacement sickle blades 18 and scaler blades 17 can be purchased when the blades 17, 18 become worn or broken.

Figure 7:
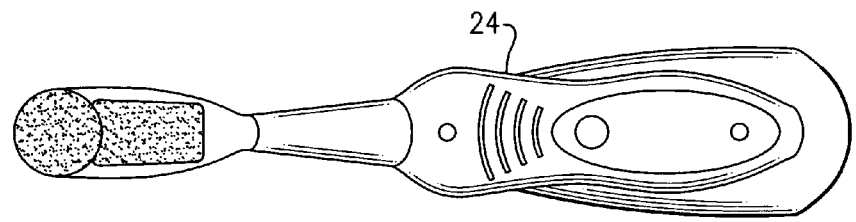
FIG. 7 is a top view of a preferred toothbrush for inclusion with the dental maintenance kit of FIG. 1A.

Referring to FIG. 7, the toothbrush 24 is shown that is included in the dental maintenance kit 10. The preferred toothbrush 24 is a battery-operated type with rotary bristles. The type of toothbrush 24 included with the dental maintenance 10 can be a basic manual type or of any other preferred design that is suitable for brushing teeth.

Figure 8:
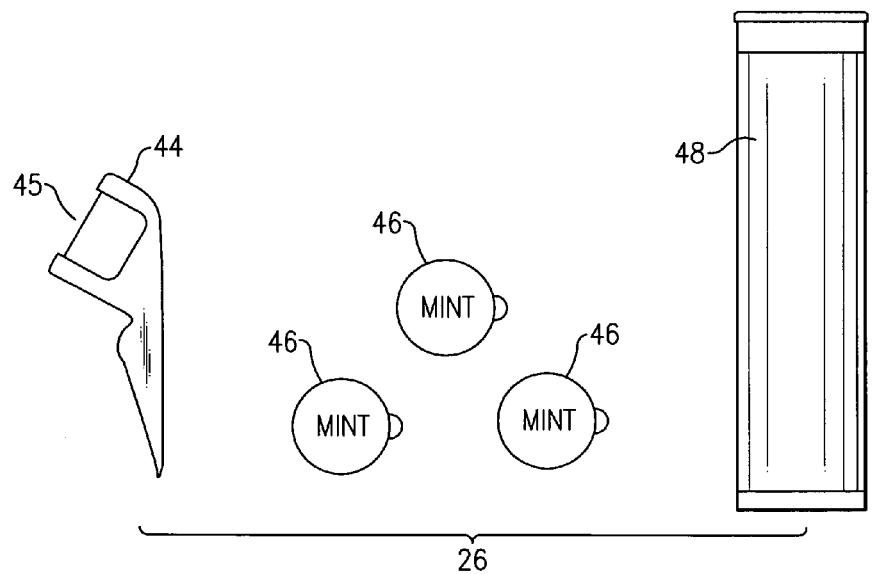
FIG. 8 is a side view of a flossing device with a plurality of pumice paste containers for inclusion with the dental maintenance kit of FIG. 1A.

Referring to FIG. 8, a plurality of flossing tools are shown removed from the plastic container 48. The flossing components included with the dental maintenance kit 10 are the flossing tool 44 with the quantity of floss 45, three containers of pumice paste 46, and the plastic storage case 48 for storage of the individual flossing components. The dimensions of the storage case 48 allow for its insertion in the fifth pocket 25 within the pouch 12 of the dental maintenance kit 10.

Referring to FIG. 9, the dental mirror 28 included in the dental maintenance kit 10 is shown. A preferred reflective surface 50 of the dental mirror 28 is a zinc crystal compound used for standard types of dental mirrors although any preferred material may be used. Inclusion of the dental mirror 28 is to provide a safe means to observe the position and the placement of the intraoral tool 16 and blades 17, 18 in order to prevent self-injury.

Referring to FIG. 10, a side view of the sickle blade 18 is shown with a detail view of the tapering of the blade 18 to a point 57. The cross sectional view in FIG. 11 taken along the line 11-11 in FIG. 10 illustrates how the sickle blade 18 is comprised of three surfaces 52, 54, 56 that taper to the point 57. The point 57 also includes three edges 57a, 57b, 57c which are used to remove plaque and debris from the inter-proximal surfaces of the teeth.

Referring to FIG. 12 a side view of the scaler blade 17 is shown illustrating how the tip of the scaler blade 17 is rounded in order to facilitate the removal of plaque and debris from the facial, buccal, mesial, and distal surfaces and from the lingual surfaces of the teeth. Referring to FIG. 13, a cross-sectional view taken along the line 13-13 in FIG. 12 shows how a working end of the scaler blade 17 is comprised of two flat surfaces 58, 60 that taper on opposite ends to an edge 61.

Figure 14:
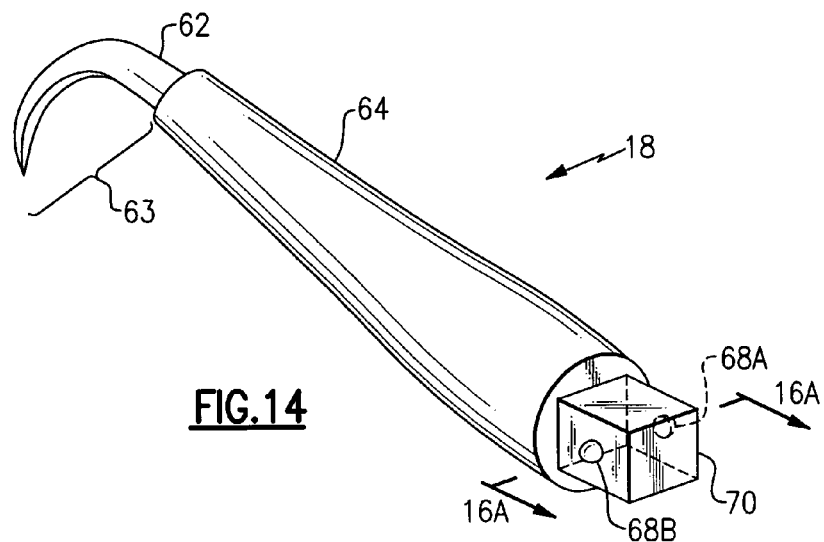
FIG. 14 is a view in perspective of a sickle blade prior to attachment to the intraoral tool of the dental maintenance kit of FIG. 1A.

Referring to FIG. 14, the sickle blade 18 is shown detached from the intraoral tool 16 that is included with the dental maintenance kit 10. The sickle blade 18 and the scaler blade 17 each attach to the intraoral tool 16 in the same way. Each sickle blade 18 and scaler blade 17 is preferably comprised of an active blade portion 62 that has a base which includes a plastic covering or coating 64 leaving exposed a working surface, identified by bracket 63, of the active portion 62. The plastic covering 64, over the lower portion of the sickle blade 18, helps to prevent an unskilled user from inadvertently cutting their gums. The plastic covering 64 extends from the working surface 63 of the sickle blade 18 where a protrusion 70 is included. The plastic covering 64 does not extend over the protrusion 70. The protrusion 70 is equipped with a pair of locking spheres 68a, 68b that are used to secure the sickle blade 18 (or scaler blade 17) to the intraoral tool 16. See also FIG. 16. The locking spheres 68a, 68b will be described in greater detail hereinafter.

Figure 15:
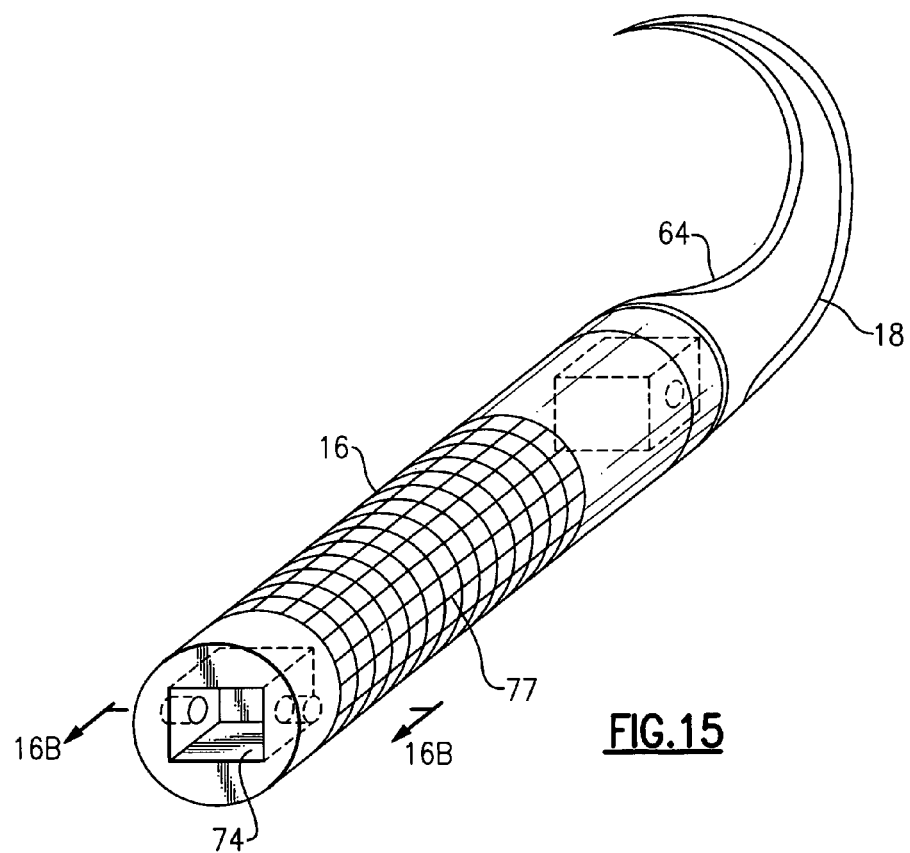
FIG. 15 is a view in perspective of the intraoral tool of the dental maintenance kit of FIG. 1A with a scaler blade attached to a distal end of the intraoral tool with a proximal end of the intraoral tool open for clarity.

Referring to FIG. 15, the intraoral tool 16 is shown with the sickle blade 18 attached at a distal end and the scaler blade 17 removed from a proximal end for clarity. A preferred material, as previously mentioned, for the intraoral tool 16 is plastic. The intraoral tool 16 preferably includes a knurled surface 77 to provide a secure grip during installation and removal of sickle blades 18 or scaler blades 17 and during use of the intraoral tool 16 while cleaning the teeth.

Referring to FIG. 16A, a cross-sectional view taken along the line 16a-16a in FIG. 14, shows how the position of the locking spheres 68a, 68b are maintained by a tension spring 72 in a channel 72a provided in the protrusion 70 that urges the locking spheres 68a, 68b within the channel 72a. The locking spheres 68a, 68b bear against a pair of tapered openings 72b at opposite ends in the channel 72a that retain position of the locking spheres 68a, 68b in the channel 72a when the sickle blade 18 (or scaler blade 17) is not attached to the intraoral tool 16.

Referring to FIG. 16B, a cross-sectional view taken along the line 16b-16b in FIG. 15, shows a receiver 74 portion integrated into the intraoral tool 16. The receiver 74 accepts the protrusion 70 of the sickle blade 18 or the scaler blade 17 when inserted into the intraoral tool 16. The blades 17, 18 are then urged in a direction shown by arrow 73 (see FIG. 16A and FIG. 16B) to lock in place. During insertion of the protrusion 70 into the receiver 74, in the direction of arrow 73, the locking spheres 68a, 68b retract into the channel 72a of the protrusion 70 and permit the protrusion 70 to enter the receiver 74. The tension spring 72 allows the locking spheres 68a, 68b to retract into the channel 72a to allow complete insertion of the protrusion 70 of the sickle blade 18 (or scaler blade 17) into the receiver 74. When the insertion of the protrusion 70 is completely seated within the receiver 74, the tension spring 72 urges the locking spheres 68a, 68b outward which secures the sickle blade 18 or the scaler blade 17 in position on the intraoral tool 16.

Referring back to FIG. 16A, removal of the sickle blade 18 (or scaler blade 17) is accomplished by applying a sufficient force to the sickle blade 18, or the scaler blade 17 in the direction of arrow 75 and simultaneously applying a force to the intraoral tool 16 in the direction of arrow 73. The opposing forces applied to the intraoral tool 16 and the sickle blade 18 (or scaler blade 17) cause the locking spheres 68a, 68b to retract into the channel 72a allowing separation of the sickle blade 18 (or scaler blade 17) from the intraoral tool 16 to occur.

The component parts that have been selected for inclusion with the dental maintenance kit 10 have been selected to compliment each other in the performance of a comprehensive teeth cleaning or routine dental maintenance. The guide 14 provides instructions for the safe and effective use of the sickle blade 18 and scaler blade 17 in addition to instructions for the use of the plurality of component parts included in the dental maintenance kit 10.

A dental maintenance kit 10 user may elect to begin with plaque removal. The basic (i.e., standard or minimum) intraoral tool 16 configuration is to attach the sickle blade 18 and scaler blade 17 on each opposite end of the intraoral tool 16. This allows the user to perform a wide range of cleaning procedures to the teeth. FIG. 10 is a side view of the sickle blade 18. The curved portion of the sickle blade 18 is comprised of the three surfaces 52, 54, 56, that taper to the point 57 as further illustrated in FIG. 11. The scaler blade 17 shown in FIG. 12 is intended to be used in concert with the sickle blade 18 as part of a plaque and/or stain removal process. The scaler blade 17 is comprised of the two flat surfaces 58, 60 that taper to the edge 61 as illustrated in FIG. 13.

The variety of components and parts included in the dental maintenance kit 10 allows the user the option to perform a basic cleaning between meals by removal of debris and plaque or a more comprehensive cleaning that includes use of the flossing tool 44, and the toothbrush 24.

An unexpected benefit from the invention is a safety release feature incorporated into the design of the locking mechanism (illustrated in FIG. 16A and FIG. 16B) that is used to secure the sickle blade 18 or the scaler blade 17 to the intraoral tool 16. When excess force is applied to the intraoral tool 16 in the direction of arrow 73 in FIG. 16A such as when prying debris from under a crown or adjacent to a filling, the sickle blade 18 or scaler blade 17 will detach from the intraoral tool 16 to prevent damage to the teeth or other personal injury from occurring. This is a significant benefit unavailable with prior dental cleaning instruments.

Another unexpected benefit from the invention is derived from the compact and portable configuration of the dental maintenance kit 10. A person can effectively remove debris lodged between teeth or under the gum line while away from home. This can save the cost and inconvenience of having to make an emergency dental appointment. For example, debris lodged under a crown can inflame the gums and cause pain. Previously, this would require, an emergency dental appointment to remove the debris. With the dental maintenance kit 10, the user can safely and easily remove the debris without assistance. Of course, the services of another person will expedite the more comprehensive cleaning procedure.

Another unexpected benefit from the invention is the potential for an overall reduction of expenses related to dental appointments that would need to be scheduled to remove debris from between teeth or to remove stains to the teeth which may occur between regularly scheduled appointments.

Also the intraoral tool 16 with the sickle blade 18 and the scaler blade 17 on each opposite end of the intraoral tool 16 is not a presently known configuration.

This is because a dental hygienist will normally use tools that have a scaler blade 17 at opposite ends or a sickle blade 18 at opposite ends. That way, the speed of cleaning is increased as the experienced professional dental hygienist alternately uses opposite ends of the same tool for the same type of cleaning on the upper and lower teeth or on the lingual and exterior sides of the teeth. By providing the intraoral tool 16 that includes both the sickle blade 18 and the scaler blade 17 simultaneously on the one tool (i.e., on the intraoral tool 16), the user can with one tool clean all of the tooth surfaces and all of the inter proximal areas (both lingual and exterior).

The intraoral tool 16 can, as desired, be configured by the user so that a variety of different combinations of the sickle blade 18 and scaler blade 17 can be attached to the intraoral tool 16 to provide maximum versatility in the use of the intraoral tool 16.

A dental prophylaxis tool that includes plastic for a handle (i.e., for the intraoral tool 16) and stainless steel for the blades 18, 17 is presently not known. Dental tools that are currently available (i.e., prior art dental hygiene tools) are made entirely from stainless steel. By eliminating the use of steel for the body of the intraoral tool 16, a significant amount of steel is eliminated. This not only reduces cost but it also reduces the signature of the dental maintenance kit 10 when passing through an airport security station. Accordingly, the dental maintenance kit 10 does not appear as if it is a weapon and so it is not likely to become an issue.

The removable blades 17, 18 of the intraoral tool 16 allow for quick and easy replacement by the user. This helps permit more rapid dental cleaning.

A dental tool with the sickle blade 18 and the scaler blade 17 that includes a plastic coating which exposes only the working surfaces 63 of the sickle blade 18 or the scaler blade 17 is presently not known. Known intraoral tools with a sickle blade 18 or a scaler blade 17 do not include a plastic safety coating 64 that is applied to the blade shaft or base. Some intraoral tools may include a plastic safety cap in the form of a small diameter tube placed over the working surface of the blade. This aforementioned safety cap must be removed prior to tool use and does not provide protection to gums and surrounding tissue during the cleaning process. This is especially important as it helps prevent an unskilled user from inadvertently cutting their gums while cleaning their own teeth.

Intraoral tools with accompanying printed instructions for use of the tools by an unskilled person are presently not known. Current intraoral tools are packaged with the assumption that purchase will be by a qualified dentist who would not require printed instructions.

If desired, other component parts may also be included in the dental maintenance kit 10. For example, a tongue scraper (not shown) and/or a cheek retractor (not shown) could also be included in the dental maintenance kit 10.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A dental maintenance kit, comprising:
   (a) a storage container;
   (b) an intraoral tool, wherein said intraoral tool includes a handle having a longitudinal length and a pair of opposite ends, and wherein each of said opposite ends includes means for detachably-attaching a sickle blade or a scaler blade to each of said opposite ends;
   (c) at least one sickle blade and at least one scaler blade for use with said intraoral tool, and wherein said at least one sickle blade, or said at least one scaler blade, or both said at least one sickle blade and said at least one scaler blade is detachably-attachable with respect to either of said opposite ends;
   (d) wherein said means for detachably-attaching a sickle blade or a scaler blade to each of said opposite ends includes a safety release that permits detachment of said sickle blade or said scaler blade apart from said intraoral tool when a sufficient force is applied to said intraoral tool that is urging said intraoral tool in a direction that is away from said sickle blade or away from said scaler blade, and
   (e) wherein said storage container is able to contain said intraoral tool and said at least one sickle blade and said at least one scaler blade.

2. A dental maintenance kit, comprising:
   (a) a storage container;
   (b) an intraoral tool, wherein said intraoral tool includes a handle having a longitudinal length and a pair of opposite ends, and wherein each of said opposite ends includes means for detachably-attaching a sickle blade or a scaler blade to each of said opposite ends, and wherein said handle is formed of a non-metallic material;
   (c) at least one sickle blade and at least one scaler blade that each include corresponding attachment means for cooperating with said means for detachably-attaching said at least one sickle blade or said at least one scaler blade;
   (d) wherein said means for detachably-attaching a sickle blade or a scaler blade to each of said opposite ends includes a safety release that permits detachment of said sickle blade or said scaler blade apart from said intraoral tool when a sufficient force is applied to said intraoral tool that is urging said intraoral tool in a direction that is away from said sickle blade or away from said scaler blade, and
   (e) wherein said storage container is able to contain said intraoral tool and said at least one sickle blade and said at least one scaler blade.

3. The dental maintenance kit of claim 2 wherein said means for detachably-attaching a sickle blade or a scaler blade to each of said opposite ends includes providing a recess in each of said opposite ends of said intraoral tool.

4. The dental maintenance kit of claim 3 wherein said recess includes a generally square or rectangular cross-sectional shape and a predetermined depth into each of said opposite ends, and wherein said recess includes an indentation that is provided along at least one of four sides of said recess.

5. The dental maintenance kit of claim 3 wherein said corresponding attachment means of said scaler blade and said sickle blade include a protrusion that is attached to a non-working end of said sickle blade and said scaler blade, and wherein said protrusion is able to be urged inside of said recess of said intraoral tool.

6. The dental maintenance kit of claim 4 wherein said corresponding attachment means of said scaler blade and said sickle blade include a protrusion that has a generally square or rectangular cross-sectional shape and which is attached to a non-working end of said sickle blade and said scaler blade, and wherein said protrusion is able to be urged inside of said recess of said intraoral tool, and wherein said protrusion includes at least one locking sphere, and wherein a force is applied to said at least one locking sphere that urges a portion of said at least one locking sphere beyond a planar surface of said protrusion, and wherein said at least one locking sphere is able to be urged into said protrusion an amount sufficient to permit insertion of said protrusion into said recess, and wherein when said protrusion is fully inserted into said recess, said portion of said at least one locking sphere is urged beyond said planar surface of said protrusion an amount sufficient for said portion of said at least one locking sphere to enter into said indentation an amount sufficient to secure said protrusion in said recess.

7. The dental maintenance kit of claim 6 wherein when said scaler blade or said sickle blade is attached to said intraoral tool and a sufficient force is applied to said intraoral tool in a first direction that is away from said scaler blade or said sickle blade and a sufficient force is applied to said scaler blade or said sickle blade in an opposite second direction, said at least one locking sphere is able to be urged into said protrusion an amount sufficient to permit release of said scaler blade or said sickle blade from either of said opposite ends of said intraoral tool.

8. The dental maintenance kit of claim 2 including an instruction guide that provides instructions sufficient to permit an unskilled user to safely use said intraoral tool and said sickle blade or said scaler blade when attached to said intraoral tool.

9. The dental maintenance kit of claim 2 including a toothbrush.

10. The dental maintenance kit of claim 9 wherein said toothbrush includes an electric type of toothbrush.

11. The dental maintenance kit of claim 10 wherein said electric type of toothbrush includes a battery-operated type of electric toothbrush.

12. The dental maintenance kit of claim 2 including dental floss.

13. The dental maintenance kit of claim 2 including a dental floss-holding device and at least one container of a preferred type of dental pumice paste or a preferred type of a toothpaste.

14. The dental maintenance kit of claim 2 including a dental mirror.

15. The dental maintenance kit of claim 2 including at least one replacement sickle blade or at least one replacement scaler blade.

16. The dental maintenance kit of claim 2 including a closeable pocket for the storage of at least one replacement sickle blade or at least one replacement scaler blade.

17. The dental maintenance kit of claim 2 wherein said storage container includes a flexible material and wherein said storage container is able to be disposed in a first, open position that permits access to an interior of said storage container and in a second, closed position that does not permit access to said interior of said storage container.

18. A dental maintenance kit, comprising:
(a) a storage container;
(b) an intraoral tool, wherein said intraoral tool includes a handle having a longitudinal length and a pair of opposite ends, and wherein each of said pair of opposite ends includes means for detachably-attaching a sickle blade or a scaler blade to each of said pair of opposite ends; and wherein said handle is formed of a non-metallic material;
(c) wherein said means for detachably-attaching a sickle blade or a scaler blade to each of said opposite ends includes a safety release that permits detachment of said sickle blade or said scaler blade apart from said intraoral tool when a sufficient force is applied to said intraoral tool that is urging said intraoral tool in a direction that is away from said sickle blade or away from said scaler blade;
(d) at least one sickle blade and at least one scaler blade that each include corresponding attachment means for cooperating with said means for detachably-attaching said at least one sickle blade or said at least one scaler blade and wherein said sickle blade or said scaler blade or both said sickle and said scaler blade is detachably-attachable with respect to either of said opposite ends;
(e) an instruction guide that provides instructions sufficient to permit an unskilled user to safely use said intraoral tool and said sickle blade or said scaler blade when attached to said intraoral tool;
(f) a toothbrush;
(g) a preferred type of dental pumice paste or a preferred type of a toothpaste;
(h) a dental mirror; and
(i) wherein said storage container is able to contain said intraoral tool, said at least one sickle blade, said at least one scaler blade, said instruction guide, said toothbrush, said preferred type of dental pumice or said preferred type of toothpaste, and said dental mirror.

* * * * *